United States Patent
Kruger (10) Patent No.: US 9,618,481 B2
(45) Date of Patent: Apr. 11, 2017

(54) ULTRASONIC TRANSDUCER ASSEMBLY AND SYSTEM FOR MONITORING STRUCTURAL INTEGRITY

(75) Inventor: Silvio E. Kruger, Brossard (CA)

(73) Assignee: National Research Council of Canada, Ottawa (CA)

( * ) Notice: Subject to any disclaimer, the term of this patent is extended or adjusted under 35 U.S.C. 154(b) by 177 days.

(21) Appl. No.: 13/883,473

(22) PCT Filed: Nov. 7, 2011

(86) PCT No.: PCT/CA2011/001234
§ 371 (c)(1),
(2), (4) Date: May 3, 2013

(87) PCT Pub. No.: WO2013/063676
PCT Pub. Date: May 10, 2013

(65) Prior Publication Data
US 2014/0182382 A1    Jul. 3, 2014

Related U.S. Application Data (60) Provisional application No. 61/410,473, filed on Nov. 5, 2010.

(51) Int. Cl.
*B01B 1/06*    (2006.01)
*G01N 29/24*   (2006.01)
(Continued)

(52) U.S. Cl.
CPC ............... *G01N 29/24* (2013.01); *B01B 1/06* (2013.01); *B23P 11/00* (2013.01); *G01N 29/228* (2013.01);
(Continued)

(58) Field of Classification Search
CPC ........ B06B 1/06; B06B 1/0603; B06B 1/0607
(Continued)

(56) References Cited

U.S. PATENT DOCUMENTS 3,242,723 A    3/1966  Evans et al.
3,781,576 A    12/1973 Runde et al.
(Continued)

FOREIGN PATENT DOCUMENTS

CA    2667751    5/2008
CA    2459921    12/2009
(Continued)

OTHER PUBLICATIONS

Kobayashi et al (2006) Flexible Ultrasonic Transducers, IEEE Transactions on Ultrasonics, Ferroelectrics, and Frequency Control, vol. 53, No. 8, p. 1478-1486.
(Continued)

*Primary Examiner* — Derek Rosenau
(74) *Attorney, Agent, or Firm* — Adam J. Cermak; Cermak Nakajima & McGowan LLP (57) ABSTRACT

In an ultrasonic transducer assembly, a conformable ultrasonic transducer has a piezoelectric layer and electrodes able to conform to curved surfaces, and a clamp for pressing the transducer into ultrasonic contact with a curved surface. Conformability is ensured with a thin, porous piezoelectric layer and suitable electrical conductors and insulators. The ultrasonic transducer may operate without further thermal shielding under harsh environments and/or at high temperatures.

17 Claims, 4 Drawing Sheets

(51) Int. Cl.
*G01N 29/28* (2006.01)
*G01N 29/22* (2006.01)
*B23P 11/00* (2006.01)

(52) U.S. Cl.
CPC .......... *G01N 29/245* (2013.01); *G01N 29/28* (2013.01); *G01N 2291/0258* (2013.01); *G01N 2291/265* (2013.01); *G01N 2291/2634* (2013.01); *Y10T 29/49966* (2015.01)

(58) Field of Classification Search
USPC .................................................. 310/322, 334
See application file for complete search history.

(56) References Cited

U.S. PATENT DOCUMENTS

| | | | |
|---|---|---|---|
| 3,987,674 A | 10/1976 | Baumoel | |
| 4,216,403 A * | 8/1980 | Krempl et al. | 310/334 |
| 4,304,126 A | 12/1981 | Yelke | |
| 4,333,352 A | 6/1982 | Connery et al. | |
| 4,392,380 A | 7/1983 | Caines | |
| 4,462,092 A | 7/1984 | Kawabuchi et al. | |
| 4,567,770 A | 2/1986 | Rumbold et al. | |
| 4,735,097 A | 4/1988 | Lynnworth | |
| 4,738,737 A | 4/1988 | Runde et al. | |
| 4,783,997 A | 11/1988 | Lynnworth | |
| 5,166,573 A | 11/1992 | Brown | |
| 5,214,343 A | 5/1993 | Baumoel | |
| 5,325,012 A | 6/1994 | Sato et al. | |
| 5,354,220 A | 10/1994 | Ganguly et al. | |
| 5,426,980 A | 6/1995 | Smith | |
| 5,463,905 A | 11/1995 | Baird | |
| 5,711,058 A | 1/1998 | Frey | |
| 5,810,009 A | 9/1998 | Mine et al. | |
| 5,886,456 A | 3/1999 | Stubbs et al. | |
| 5,922,961 A | 7/1999 | Hsu et al. | |
| 6,255,761 B1 | 7/2001 | Benjamin | |
| 6,532,827 B1 | 3/2003 | Ohnishi | |
| 6,543,299 B2 | 4/2003 | Taylor | |
| 6,634,071 B2 | 10/2003 | Benjamin | |
| 6,711,096 B1 | 3/2004 | Benjamin | |
| 7,185,547 B2 | 3/2007 | Baumoel | |
| 7,415,893 B2 | 8/2008 | Takeda et al. | |
| 7,569,975 B2 | 8/2009 | Nye et al. | |
| 7,703,337 B1 | 4/2010 | Feller | |
| 7,741,756 B2 | 6/2010 | Sudol | |
| 7,743,659 B2 | 6/2010 | Kearns et al. | |
| 2005/0227538 A1 | 10/2005 | Engel | |
| 2007/0261493 A1 | 11/2007 | Kim | |
| 2009/0034370 A1* | 2/2009 | Guo | 310/334 |
| 2009/0115290 A1 | 5/2009 | Cochran et al. | |

FOREIGN PATENT DOCUMENTS

| | | |
|---|---|---|
| CA | 2745558 | 1/2012 |
| CN | 201804553 | 4/2011 |
| GB | 1475224 | 6/1977 |
| GB | 2086584 | 5/1982 |
| GB | 2282931 | 4/1995 |
| JP | 01173695 | 7/1989 |
| JP | 10-507530 | 7/1998 |
| JP | 10293124 A2 | 11/1998 |
| JP | 2001-508547 | 6/2001 |
| JP | 2007003443 A2 | 1/2007 |
| JP | 2008045989 A2 | 2/2008 |
| JP | 2003151588 | 11/2008 |
| JP | 2009212776 A2 | 9/2009 |
| JP | 2009276085 | 11/2009 |

OTHER PUBLICATIONS

Safari A. (1994) Development of piezoelectric composites for transducers, Classification Physics Abstracts, p. 1129-1149.
Advanced transducer development, Nov. 22, 2010; http://www.twi.co.uk/content/spaghapr2007.html.
Morgan Technical Ceramics; Nov. 22, 2010, http://www.azom.com/news.asp?NewsID=18871.
NDT1-220K, Nov. 22, 2010, http://www.meas-spec.com/product/t_product.aspx?id=5411.
Quickpack, Nov. 22, 2010, http://www.mide.com/products/qp/qp22b.php.
Review of progress, 1993.
BARUT, Silvere, Use of Piezoelectric Films for NDT, ECNDT 2006.
Bowen et al. 2008, Flexible piezoelectric transducer for ultrasonic inspection of non-planar components, Ultrasonics 48 p. 367-375.
ISR and WO from corresponding PCT/CA2011/001234, mailed on Feb. 22, 2012.
English translation of Abstract of CN201804533U.
English translation of Abstract of Japanese Application No. 2003151588.
English translation of Abstract of Japanese Application No. 2009276085.
IPRP from corresponding PCT/CA2011/001234, issued May 8, 2013.
Extended European Search Report for corresponding EP Application No. 11874860.7, mailed on Jul. 28, 2015.
Hartley D.P.K. et al., Ultrasonic monitoring of vessel and pipeline corrosion for the process industry—a novel approach, Institute of Measurement and Control, 1997, vol. 30, No. 5, pp. 134-137.
Notice of Reasons for Rejection issued for corresponding Japanese Application No. P2013-541159 issued on Sep. 15, 2015.
JP 2001-508547 corresponding PCT Application No. WO98/57166.
JP 10507530 corresponding PCT Application No. WO96/12951.
English Abstract for JP2008045989A2.
English Abstract for JP2009212776A2.
English Abstract for JP2007003443A2.
English Abstract for JP10293124A2.
English Abstract for JP01173695.

* cited by examiner

ULTRASONIC TRANSDUCER ASSEMBLY AND SYSTEM FOR MONITORING STRUCTURAL INTEGRITY

This application is a national phase entry of International Patent Application PCT/CA2011/001234 filed Nov. 7, 2011 and claims the benefit of United States Provisional Patent Application U.S. Ser. No. 61/410,473 filed Nov. 5, 2010, the entire contents which are herein incorporated by reference.

FIELD OF THE INVENTION

The present invention relates to an ultrasonic sensing assembly and system that is particularly useful for the monitoring of curved objects, including those that operate at high temperatures.

BACKGROUND OF THE INVENTION

Corrosion, erosion, fatigue, creep are examples of degradation mechanisms that limit the life time of structures and cause significant economic impact on many industries. The prediction of life time of structures is often not precise enough and inspection methods are regularly applied to structures to determine its health condition. Ultrasonics is one of the most valuable non-destructive testing methods to evaluate the condition of structures exposed to degradation mechanisms.

Structural health monitoring (SHM) of components of power plants, oil & gas and aerospace industries, such as pipes and other vehicle parts having respective contoured surfaces is desirable, but tricky. Access to the structural parts to be inspected may be difficult due, for example, to safety concerns for inspectors, or to a limited access to the structure surface due to thermal insulation, adjacent mechanisms, electrical, pneumatic or hydraulic control lines, etc. Furthermore, once access is provided, installing a sensor in a way that provides adequate contact between a piezoelectric material and the component to be tested, may be difficult. Also, the inspection may require the shutdown of a running process. Therefore permanently or semi-permanently installed transducers are often preferred, especially in transducers that permit a state of the structure to be sensed at any time (on demand) by electronic request. The time between inspections is typically chosen in order to provide accurate prediction of the remaining life time of the structures. Therefore permanently attached transducers with easy electronic interrogation of the sensor are in demand to make shorter and less costly interrogation of the condition of the structure.

Sensors for structural health monitoring are often required to operate in harsh environments as for example, at high temperatures. Therefore the permanently attached transducers may also be required to maintain its performance for long periods of time, at high temperatures. High temperatures transducer configurations have been proposed using a delay line and cooling of transducers as for example, in U.S. Pat. No. 7,185,547 to Baumoel, entitled "Extreme Temperature Clamp-on Ultrasonic Flowmeter Transducer". The delay lines and cooling significantly limits the value of such transducers for widespread structural health monitoring. Therefore it is required to develop transducers composed of materials that can maintain a significant proportion of its essential properties at high temperatures.

Similar techniques have been used to separate ultrasonic transducers from high temperature surfaces and the separation, though perceived to be required for operation of the sensor, impairs the use of the sensor, and occupies a lot of space around the component.

Other examples of patents in this field are: U.S. Pat. No. 3,781,576, to Runde, et al., entitled High temperature Ultrasonic Transducer; U.S. Pat. No. 4,392,380, to Caines entitled High Temperature Pressure Coupled Ultrasonic Waveguide; U.S. Pat. No. 4,567,770 to Rumbold et al., entitled Ultrasonic Transducer Apparatus and Method for High Temperature Measurements; U.S. Pat. No. 4,738,737 to Runde et al., entitled Method of Using a High Temperature Ultrasonic Couplant Material; U.S. Pat. No. 4,783,997, to Lynnworth entitled Ultrasonic Transducers for High Temperature Applications; U.S. Pat. No. 5,325,012 to Sato et al., entitled Bonded Type Piezoelectric Apparatus, Method for Manufacturing the Same and Bonded Type Piezoelectric Element; U.S. Pat. No. 5,886,456 to Stubbs et al., entitled Ultrasonic Transducer and Ultrasonic Detection and High Temperature Processing Systems Incorporating Same; and U.S. Pat. No. 7,743,659 to Kearns et al., entitled Structural Health Monitoring (SHM) Transducer Assembly and System.

Figure 1:
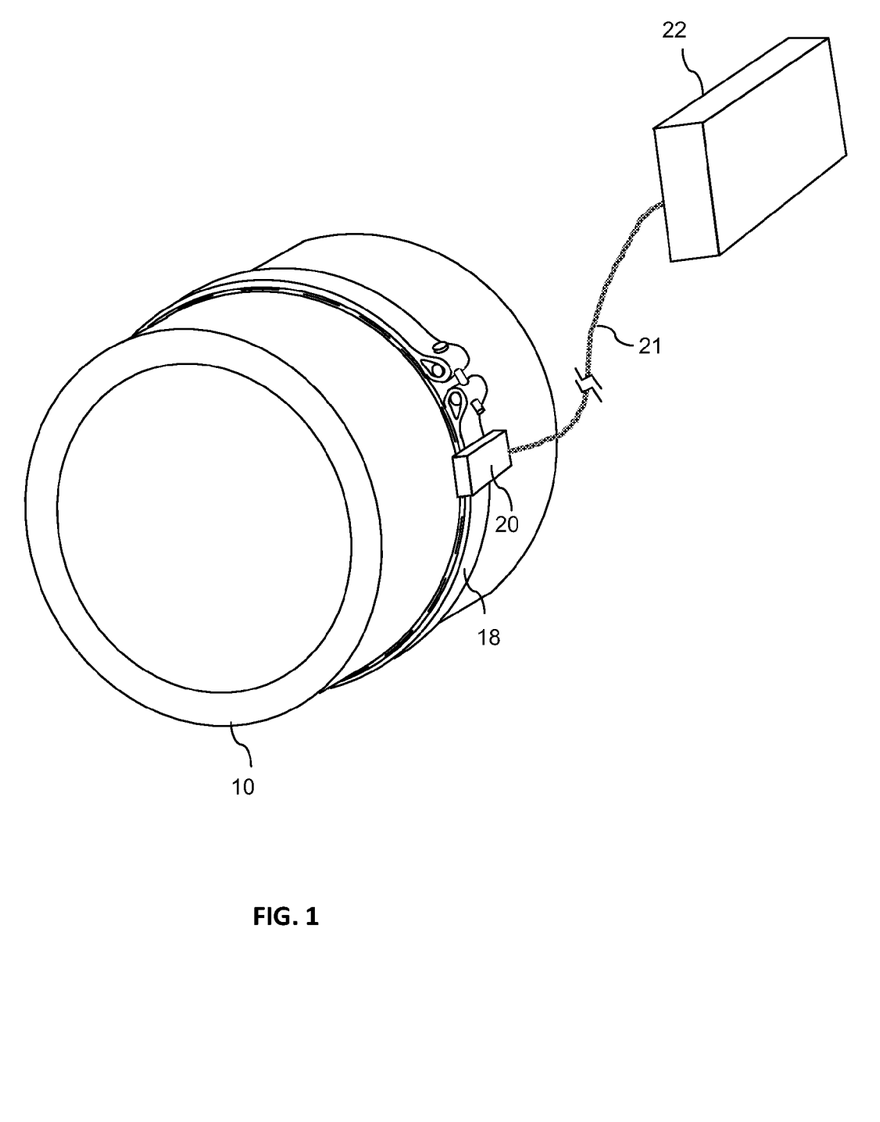
FIG. 1 shows a perspective view of a clamp-on multi-element transducer array according to an embodiment of the present invention.
Figure 2:
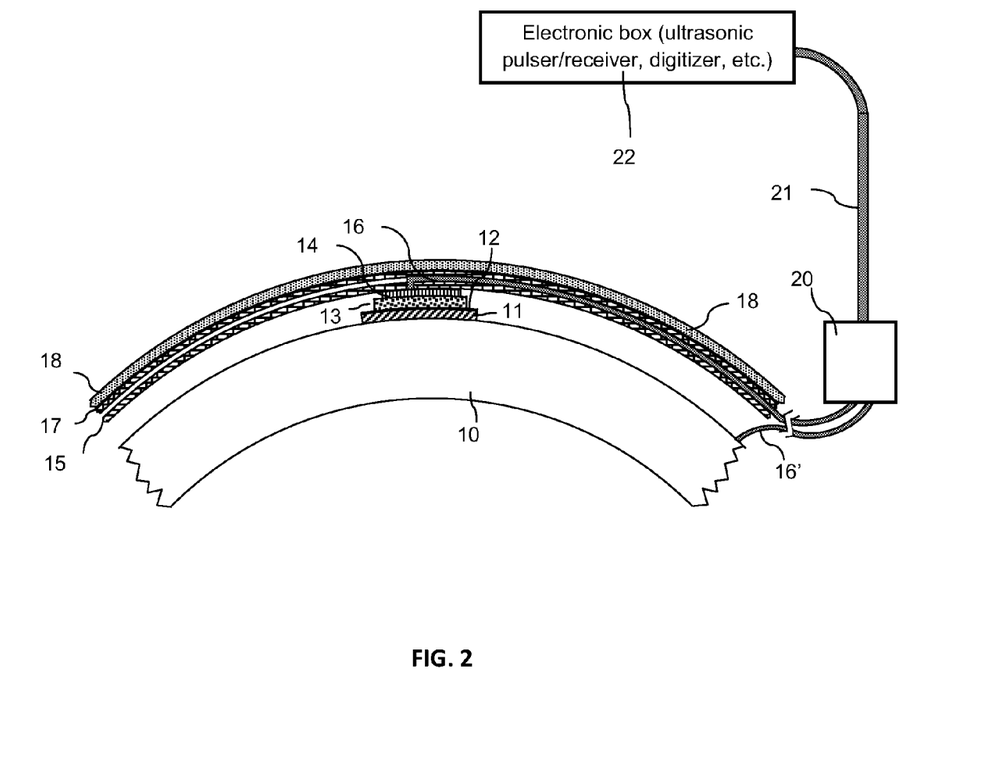
FIG. 2 shows a partial cross-sectional view of a single-element transducer assembly according to an embodiment of the present invention.

"Flexible Ultrasonic Transducers" by Kobayashi, M., Jen, C. K, and Levesque, D., IEEE Trans. on Ultrasonics, Ferroelectrics and Frequency Control, vol. 53, no. 8, August 2006 teaches that the flexible ultrasonic transducers (FUTs) are applicable to in-situ SHM, NDT and on-line diagnosis. To demonstrate the flexibility and operability of such FUTs when flexed, one experiment was performed on a thick pipe at room temperature and at elevated temperatures. As shown in FIG. 1, and FIG. 2, a viscous oil ultrasonic couplant was applied on the pipe at the location of testing, it was covered with a 75 micron stainless steel foil, and a PZT piezoceramic film, which was topped with a silver paste, to serve as an electrode. The pipe itself served as the ground. A mechanical holder is provided to maintain the FUT in place.

While the mechanical holder of Kobayashi et al. encircled a pipe, it was not a clamp for the FUT as the term is used in the present art, and the active area of the FUT is substantially free of pressure as there is a wide opening in the clamp surrounding the FUT, as is shown in FIGS. 1 and 2. The purpose of the clamp is just to prevent slipping of the FUT on the oiled, rounded, surface. Also in this previous art, the electrical connections are made by spring-loaded pins that are not practical for real industrial applications.

Other previous art that uses some kind of flexible transducers like U.S. Pat. No. 5,166,573 to Brown, for example, which teaches how to produce polymer-base FUTs and flexible UT arrays, but does not teach a practical assembly to attach to permanently monitor structures. Also, as the piezoelectric layers of these transducers are polymer-based, they are inherently incapable of high temperature applications.

Accordingly, there is a need for improved ultrasonic transducer assemblies to perform structural health monitoring that can be permanently installed in curved objects, can maintain performance for long periods of time, including at high temperatures and harsh environments, and can allow easy and automated electronic interrogation of the condition of the structure.

BRIEF SUMMARY OF THE INVENTION

A transducer assembly is provided for structural health monitoring, and the like, that improves the durability and signal quality while avoiding difficulties characterized with the prior art. While one substantial advantage of using a clamp is that substantially higher pressures can be applied, allowing a greater variety of couplants to be used for higher temperature applications, for example, the clamp with a flexible piezoelectric film has advantages even in low temperature applications without any couplant, improving durability of the transducer assembly, avoiding debonding, and improving signal quality and strength.

Accordingly, an ultrasonic transducer assembly is provided that includes a piezoelectric film that is able to conform to curved surfaces, at least a flexible electrode adjacent to a top surface of the piezoelectric film, to make the piezoelectric film able to act as an ultrasonic transducer, a flexible insulating layer covering the top electrode and at least part of a first electrical connector extending from the top electrode to an electronic control, the insulating layer having a shape and size to substantially surround a section of a component to be monitored, and a permanent or semi-permanent clamp adapted to apply at least a 0.2 MPa compressive stress on a region of the component aligned with the top electrode. The clamping of the FUT in the region aligned with the top electrode ensures that the stress is applied where the contact is needed to improve ultrasonic coupling between the FUT and the section of the component.

The transducer assembly is preferably flexible so that it may be clamped to curved surfaces, such as pipes, or pipe fittings (e.g. elbows, couplers, pipe joints, etc.) and other shaped components, especially those components that have sections that include convex surfaces. The materials chosen for construction of the transducer assembly may retain sufficient structural, electrical, and chemical integrity under severe harsh environments, such as high temperatures, making the assembly suitable for high temperature operation. For example, the piezoelectric film may have a composition consistent with fabrication using one or more layers of a mixture of a piezoelectric powder and organic precursors of dielectric and/or piezoelectric material. The resulting piezoelectric film may therefore have a level of porosity that improves flexibility, resistance to thermal shock and ultrasonic bandwidth.

The transducer assembly may further comprise an ultrasonic coupling layer (or couplant) composed of an ultrasonic transmitting material that makes an intimate physical contact with the transducer assembly, for making intimate physical contact with the component to be monitored. The couplant may comprise a high temperature paste or liquid, or a soft metal, such as aluminum, gold, tin, zinc or other alloys known to the art of soldering and brazing. A foil of a soft (or temperature softened) metal may be particularly preferred for longevity of the couplant system. Some foils (such as gold) require greater stress to ensure intimate physical contact. Accordingly, if a metal foil couplant is used, the clamp may be adapted to apply at least 1 MPa compressive stress, or at least 10 MPa compressive stress. The clamp may be adapted to apply an initial compressive stress greater than 1 MPa to plastically deform the metal foil, and a far lower compressive stress thereafter for maintaining the intimate physical contact. The metal foil may have been strained by a much greater compressive stress than the clamp, in which case the clamp may serve only to maintain intimate physical contact between the assembly and the component.

The assembly may further comprise a bottom electrode adjacent the piezoelectric film on a surface opposite the top electrode. The bottom electrode may be electrically coupled to the component, which is sufficiently conductive to serve as a ground for the flexible ultrasonic transducer, or coupled to the electronic control by a second electrical connector that is insulated from the first electrical connector. The bottom electrode may also serve as the clamp.

The insulating layer may include a conductive path between top and bottom insulations, with a via through the bottom insulation for providing electrical contact between the conductive path and the top electrode. The insulating layer may be formed of mica or polyimide.

The piezoelectric layer may be bonded to the component to be monitored by a ceramic binder made from organic precursors of a piezoelectric and/or dielectric ceramic.

A protective layer may surround the insulating layer. The clamp may be a band that serves as the protective layer. The clamp may be a tube clamp, comprising a deformable band for surrounding the section, formed of metal or a fibreglass textile, and may have a tensioning mechanism with a spring or spring washer to maintain a constant tension under different thermal conditions. More deformable band materials have superior conformability making them suited to components having more complex geometry.

A plurality of separate piezoelectric films may be spaced along the insulating layer to provide a transducer array, each piezoelectric film being similar. The separate piezoelectric films are independently electronically addressable by the electronic control, or are commonly electronically controlled.

Accordingly a method is provided for producing a transducer assembly. The method comprises providing a flexible ultrasonic transducer, including at least a top electrode adjacent to a flexible piezoelectric film; bonding said top electrode to an insulating layer, the insulating layer having a shape and size to substantially surround a section of a component to be monitored, providing insulated electrical connection from the top electrode to an electronic control, and providing a permanent or semi-permanent clamp adapted to apply at least a 0.2 MPa compressive pressure on a region of the component aligned with the top electrode.

The method may further comprise preparing a part of a surface of the section of the component; applying a couplant to the part of the surface to provide intimate physical contact between the couplant and the surface; and mounting the previously assembled layers to the couplant to provide intimate physical contact between the couplant and the flexible ultrasonic transducer. If the couplant is in the form of a metal foil, the mounting may comprise applying an initial compressive stress greater than 1 MPa to plastically deform the soft metal foil. Alternatively, applying the couplant may comprise applying an adhesive material, such as a polymer based glue, silver paste, ceramic cement, glass known in the art of adhesive bonding.

If the couplant or the component is not electrically conductive, the method may further comprise applying a bottom electrode and insulated conductors from the bottom electrode to the electrical control. The bottom electrode may be a titanium, aluminum or stainless steel foil, or other metal or metalized foil.

Providing the flexible ultrasonic transducer may comprise applying one or more layers of a mixture of a piezoelectric powder and organic precursors of dielectric and/or piezoelectric material; heat treating the applied layers; and poling the applied layers to produce the piezoelectric film, and may further comprise applying the top electrode as a silver or gold paste or by thin film deposition of a conductive metal, such as gold, silver, platinum or aluminum. Alternatively the flexible ultrasonic transducer may be provided as a separate component, or may be integrated with the insulating layer.

The electrical control may comprise an electric pulse generator, an electric signal detector, an electrical analog to digital signal converter, a digital memory, and a communications interface for exchanging digitized signals by conductor or wirelessly.

BRIEF DESCRIPTION OF THE DRAWINGS

Preferred embodiments of the invention can be understood in more detail from the following descriptions taken in conjunction with the accompanying drawings in which.

DETAILED DESCRIPTION OF THE PREFERRED EMBODIMENT

The following detailed description of embodiments refers to the accompanying drawings, which illustrate specific embodiments of the invention. This invention may, however, be embodied in different forms and should not be construed as limited to the embodiments set forth herein.

FIG. 1 is a schematic illustration of an example of the embodiment of multi-element ultrasonic transducer assembly for monitoring structural integrity. In this example a tube clamp 18 is used as a mechanically constraining layer. It embraces all other layers of the assembly and makes a robust attachment to the component to be monitored 10 represented by a tube in this example. Tube clamp 18 ensures good physical contact between layers of the transducer assembly where ultrasound need be transmitted. The transducer assembly is mounted on a pipe. Other common examples of components to be monitored include pipe fittings, and pressure vessels among others. In this example, a connection box 20 is used to connect electrical conductors of the transducer assembly array to an external multi-conductor cable 21 that is to be connected to an electronic control 22. In another embodiment, each conductor of the external multi-conductor cable 21 continues to each element of the transducers and the connection box 20 is not necessary.

FIG. 2 is a schematic illustration of a cross-sectional detailed view of a part of an ultrasonic transducer assembly in accordance with an embodiment of the present invention, having a single piezoelectric element. It will be noted that the extreme thinness of some of the layers make them ill suited for scaled representation. For example, the electrodes may be hundreds of nanometers thick, the piezoelectric layers and electrical foils may be microns thick, insulating layers may be hundreds of microns thick, and the tube clamp band may be a few millimeters thick or thinner, in typical examples.

In this embodiment, a piezoelectric film 13, located between a top electrode 14 and a bottom electrode 12, is driven by an electric excitation carried by electric conductors 16 and 16'. The piezoelectric film 13, in this embodiment, has preferably some flexibility in order to bend to fit curved objects, even if it was formed by in-situ deposition. The piezoelectric film 13 preferably has some internal damping to avoid the need for a backing, while still being able to excite and detect short ultrasonic pulses. If the transducer assembly is to be used to monitor components at high temperature, it is preferable that the piezoelectric film 13 show good resistance to thermal expansion of both top electrode 14 and bottom electrode 12. The piezoelectric layer 13 may be made of materials that maintain piezoelectricity at high temperatures. These properties for a piezoelectric film can be obtained, for example, by producing it by the method known in the art as the sol-gel route. Both the top electrode 14 and bottom electrode 12 are preferably thin compared to the ultrasonic wavelength in order to avoid spurious echoes. Thin electrodes have also, in general, the advantage of being flexible, which allows them to be fitted to curved surfaces. Electric conductors 16,16' connect the top and bottom electrodes to the electronic control 22, and are electrically separated from other electric conductive parts of the assembly by the top insulator 17 and bottom insulator 15. The connection to the bottom electrode 16', often referred to as the ground, can be connected to the component 10, provided that it is electrically conductive and the bottom electrode is connected to the component 10. In some embodiments, it may be preferable to use a connection box 20 between the electric conductors 16,16' of the transducer assembly and the electronic control 22. In such cases, appropriate conductive cables 21 connect the electronic control 22 to the connection box 20. The electrical conductors 16,16' can be in the form of wire or a foil strip or any other electrical conductor means known in the art. The electric insulation layers 15 and 17, are preferably of a flexible material, to conform to a component with curved surfaces, while maintaining its properties at high temperatures (if the component 10 is monitored at high temperature). Materials that are known to be suitable for insulator layers include mica, fibreglass textiles and polyimide, among others. To hold this ultrasonic transducer assembly layers 12-17 to the component 10, the clamp 18 is provided. The clamp 18 applies a stress that keeps the layers in intimate physical contact with each other and the component 10. At the same time, the clamp 18 protects the assembly against external aggression.

The ultrasonic excitation generated by the piezoelectric layer 13 is typically better transmitted to the component 10 via a coupling layer 11. The coupling layer 11 may be a liquid, gel, or solid and should be preferably thin compared to the wavelength of ultrasonic wave generated by the piezoelectric layer. Some materials that may be used as an coupling layer include ultrasonic liquid couplants, polymeric adhesive materials, silver and gold paste, soft metal foils like gold, aluminum, zinc and tin as well as low melting temperature metals like aluminum, zinc, tin and other alloys known in the art of soldering and brazing.

To facilitate installation of the ultrasonic transducer assembly of the present invention to component 10, the layers 12 to 18 may be preferred to be preassembled in a manufacturing facility. The preassembled transducer is them installed to the component to be monitored 10 after preparing its surface, if needed, and applying the coupling layer 11. Some coupling layers solutions may need a thermal treatment to obtain the desired properties, and some operate only at certain temperatures.

Figure 3:
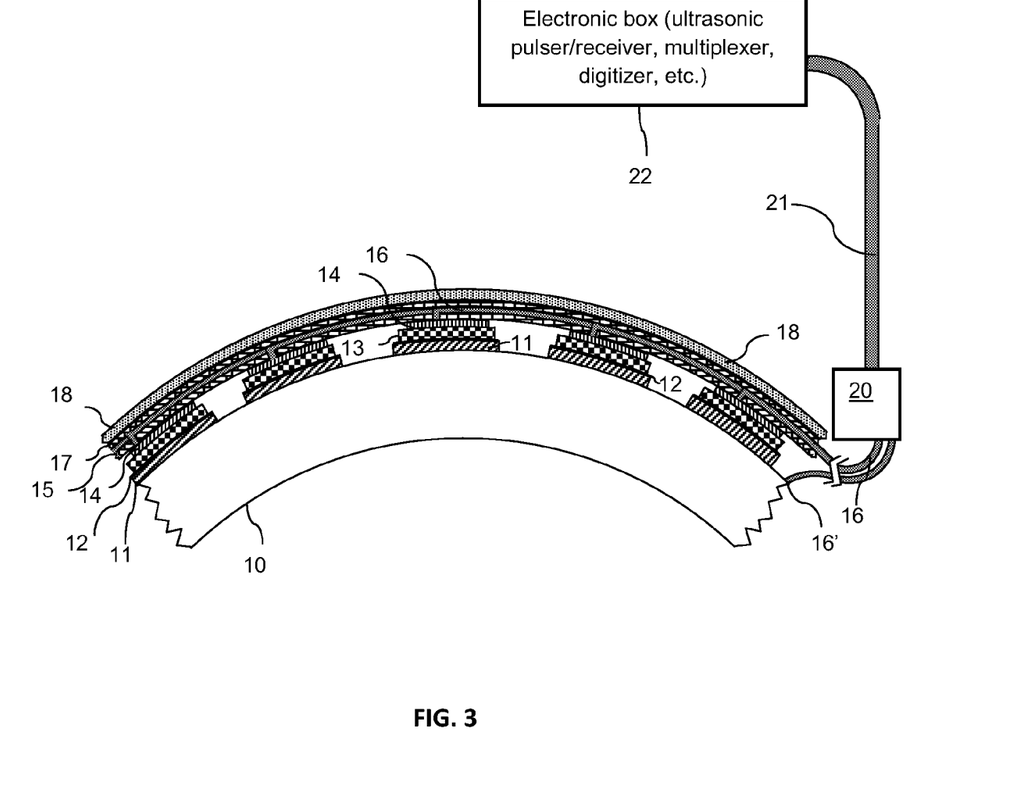
FIG. 3 shows a partial cross-sectional view of a multi-element transducer assembly according to an embodiment of the present invention.

A multi-element ultrasonic transducer assembly can also be of interest. FIG. 3 shows an example of an embodiment, which is similar to a one-element configuration shown in FIG. 2 but have many elements along the component 10. The electrical conductor 16 in this embodiment connect the top electrode 14 of each element of transducer subassembly independently of the connection box 20 allowing independent ultrasonic operation for each element. The bottom electrode connection 16', or ground connection, is common for all elements. It will be noted that independently addressable elements may be desired for different purposes, and parallel insulated conductors between the top and bottom insulating layers 15,17 can be provided.

There are many configurations for layers of the ultrasonic transducer assembly of this invention that can conform to curved surfaces of the component to be monitored. The transducer assembly configuration shown in FIG. 4A as an enlarged cross-sectional view, is similar to those already described in FIG. 2 and FIG. 3 with a coupling layer 11, making intimate contact to the component 10 and the bottom electrode 12. The piezoelectric layer 13 is in intimate physical contact with bottom electrode 12 and the top electrode 14. The electrical conductor 16 is in conductive contact with the top electrode 14 at one of its ends through a hole in the bottom insulator 15, and at the other of its ends, at the connection box 20 or the electronic control 22 (depending on the control arrangement chosen). Two insulator layers, the bottom insulator layer 15 and top insulator layer 17 may be used to insulate the electrical conductor 16 from other conductive parts of the assembly.

Figure 4A:
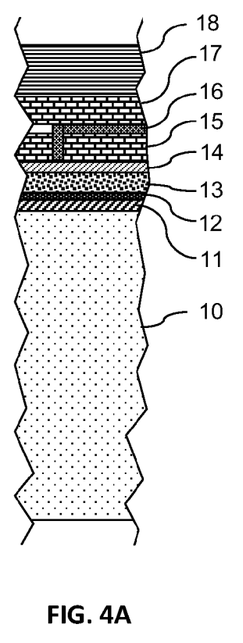
FIG. 4A shows a partial cross-sectional view of an example lay-up configuration for forming the transducer assembly according to an embodiment of the present invention.

Alternatively a single top insulator could be used, with an alternative insulation provided, to the extent needed. Clamp 18 keeps the layers that need intimate physical contact together, and at the same time, may protect the assembly against external aggression.

Figure 4B:
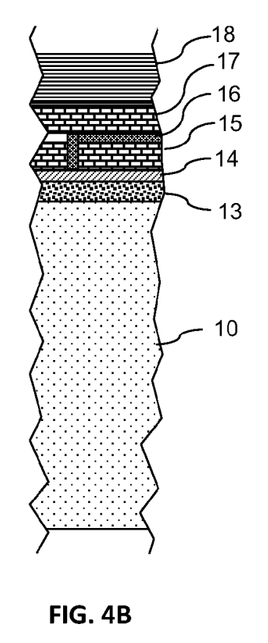
FIG. 4B shows a partial cross-sectional view of another example lay-up configuration for forming the transducer assembly according to an embodiment of the present invention.

Another transducer assembly configuration is shown in FIG. 4B with an enlarged cross-sectional view. Similar reference numerals denote analogous elements, and their description is not repeated herein. In this case, the piezoelectric layer 13 is in intimate contact with the component 10. This intimate contact can be obtained by the fabrication of the piezoelectric film 13 directly on the surface of component 10 or alternatively by bonding a piezoelectric film to the component to be monitored with a binder with similar characteristics to the piezoelectric layer. In this embodiment the bottom electrode is provided by the component 10, and electrical connection with this ground plane is provided to the connection box or electrical control (not shown).

Figure 4C:
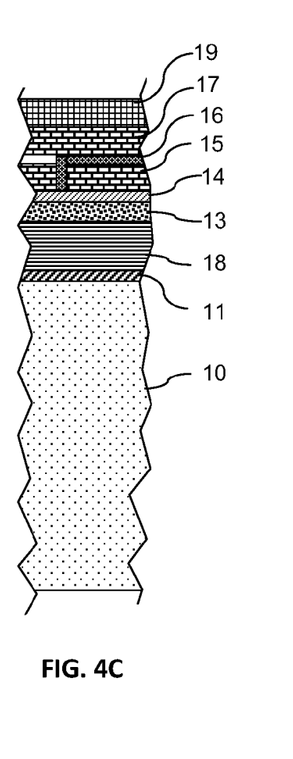
FIG. 4C shows a partial cross-sectional view of another example lay-up configuration for forming the transducer assembly according to an embodiment of the present invention.

FIG. 4C schematically illustrates an enlarged cross-sectional view of a transducer assembly in which the clamp 18 is also bottom electrode 12. In this example, the piezoelectric layer 13 is in intimate contact with the clamp 18. This configuration may be particularly useful wherein the chosen coupling layer 11 needs a higher stress mechanical constraint to make intimate physical contact with the component 10 to allow efficient transmission of the ultrasonic waves, e.g. if the surface of the component is particularly rough, or the couplant 11 is stiff. The remainder of the flexible ultrasonic transducer may be the same as above, but it may further be desirable to provide a protective layer 19, to surround the top insulating layer 17 to protect the assembly against external aggression. Protective layer 19 need not apply any appreciable pressure to the insulating layer 17.

Figure 4D:
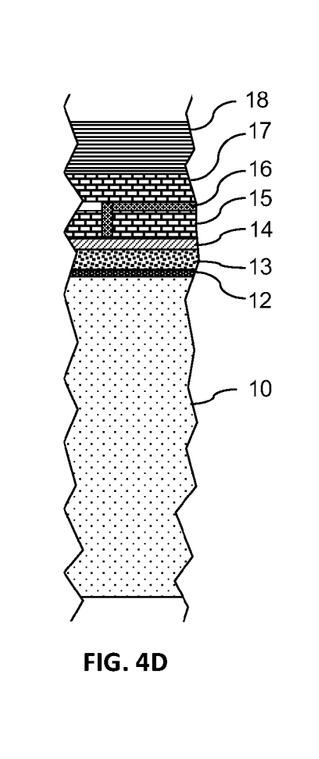
FIG. 4D shows a partial cross-sectional view of another example lay-up configuration for forming the transducer assembly according to an embodiment of the present invention.

FIG. 4D schematically illustrates an enlarged cross-sectional view of a transducer assembly having no couplant 11 other than the bottom electrode 12, that may be a soft metal foil.

What is claimed is:

1. An ultrasonic transducer assembly useful for monitoring a component having a curved outer surface, the transducer comprising:
   a piezoelectric film having top and bottom surfaces, the film having a flexibility to conform to said curved outer surface and being oriented to excite and detect ultrasonic pulses in a direction orthogonal to the film bottom surface;
   top electrode adjacent to the top surface of the piezoelectric film to make the piezoelectric film able to act as an ultrasonic transducer in said direction orthogonal to the film bottom surface when a voltage is applied to said top electrode;
   a first electrical connector extending from the top electrode;
   a flexible insulating layer covering the top electrode and at least part of the first electrical connector, the insulating layer having a shape and size to substantially surround a section of a component to be monitored; and
   a clamp configured to apply at least a 0.2 MPa compressive stress on a region of the component, the clamp being aligned with the top electrode.

2. The transducer assembly of claim 1 wherein:
   the transducer assembly is flexible, and the clamp comprises a band that, when tensioned, causes the assembly to conform to a convex surface of the section of the component.

3. The transducer assembly of claim 1 further comprising the component, which has the form of a pipe or a pipe fitting;
   wherein the transducer assembly is positioned on the component curved outer surface with the clamp holding the transducer assembly to said component curved outer surface.

4. The transducer assembly of claim 1 wherein all materials used to fabricate the assembly retain structural, electrical, and chemical integrity to operate at high temperatures.

5. The transducer assembly of claim 4 wherein the piezoelectric film has a composition consistent with fabrication using one or more layers of a mixture of a piezoelectric powder and organic precursors of dielectric and/or piezoelectric material, wherein after heat treatment the piezoelectric film has a level of porosity that provides flexibility, resistance to thermal shock and ultrasonic bandwidth.

6. The transducer assembly of claim 1 further comprising an ultrasonic coupling layer composed of an ultrasonic transmitting material making intimate physical contact with the transducer assembly at a top surface, and for making intimate physical contact with the component at a bottom surface.

7. The transducer assembly of claim 6 wherein the ultrasonic transmitting material comprises: a high temperature paste or liquid, or a soft metal.

8. The transducer assembly of claim 6 wherein the coupling layer comprises a metal foil, and wherein:
   the clamp is adapted to apply at least 1 MPa compressive stress.

9. The transducer assembly of claim 1 further comprising a bottom electrode electrically coupled to the component, which is conductive to serve as a ground for the flexible ultrasonic transducer.

10. The transducer assembly of claim 1 wherein the insulating layer comprises:
a conductive path between top and bottom insulations, with a via through the bottom insulation for providing electrical contact between the conductive path and the top electrode.

11. The transducer assembly of claim 1:
wherein a plurality of similar separate piezoelectric films are spaced along the insulating layer to provide a transducer array.

12. The transducer assembly of claim 1 wherein:
the transducer assembly is flexible, and the clamp comprises a tube clamp, comprising a deformable band for surrounding the section, formed of metal or a fibreglass textile.

13. The transducer assembly of claim 1 wherein:
the transducer assembly is flexible, and the clamp comprises a tensioning mechanism, having a spring or spring washer to maintain a constant tension under different thermal conditions.

14. The transducer assembly of claim 1 further comprising a bottom electrode electrically coupled to the electronic control by a second electrical connector that is insulated from the first electrical connector.

15. The transducer assembly of claim 1 wherein a surface of the component serves as a bottom electrode of the flexible ultrasonic transducer, and has an electrical connection to the electrical control.

16. The transducer assembly of claim 1 wherein a surface of the component serves as a bottom electrode of the flexible ultrasonic transducer, and has an electrical connection to the electrical control, and the piezoelectric layer is bonded to the component to be monitored by a ceramic binder made from organic precursors of a piezoelectric and/or dielectric ceramic.

17. The transducer assembly of claim 1 wherein the insulating layer comprises a layer of mica or polyimide.

* * * * *